(12) United States Patent
Wang et al.

(10) Patent No.: US 10,365,195 B2
(45) Date of Patent: Jul. 30, 2019

(54) PROCESS AND APPARATUS TO DETERMINE THE DEGREE OF SEPARATION OF TWO SOLUTION STREAMS

(71) Applicant: Dow Global Technologies LLC, Midland, MI (US)

(72) Inventors: Alec Y. Wang, Sugar Land, TX (US); Curvel Hypolite, Rosharon, TX (US); Jorge Rubalcaba, Pearland, TX (US); Michael J. Zogg, Jr., Houston, TX (US); Job D. Guzman, Houston, TX (US)

(73) Assignee: Dow Global Technologies LLC, Midland, MI (US)

( * ) Notice: Subject to any disclaimer, the term of this patent is extended or adjusted under 35 U.S.C. 154(b) by 205 days.

(21) Appl. No.: 14/915,921

(22) PCT Filed: Nov. 25, 2014

(86) PCT No.: PCT/US2014/067461
§ 371 (c)(1),
(2) Date: Mar. 2, 2016

(87) PCT Pub. No.: WO2015/081119
PCT Pub. Date: Jun. 4, 2015

(65) Prior Publication Data
US 2016/0282251 A1    Sep. 29, 2016

Related U.S. Application Data

(60) Provisional application No. 61/909,442, filed on Nov. 27, 2013.

(51) Int. Cl.
*G01N 9/32* (2006.01)
*C08F 6/00* (2006.01)
*C08F 6/12* (2006.01)

(52) U.S. Cl.
CPC ............... *G01N 9/32* (2013.01); *C08F 6/003* (2013.01); *C08F 6/12* (2013.01)

(58) Field of Classification Search
CPC . C08L 23/00; C08F 6/003; C08F 6/12; G01N 9/32
See application file for complete search history.

(56) References Cited

U.S. PATENT DOCUMENTS

| 4,689,989 A * | 9/1987 | Aslesen ............... G01F 1/86 73/61.44 |
| 7,163,989 B2 | 1/2007 | Friedersdorf |

(Continued)

FOREIGN PATENT DOCUMENTS

| WO | 2013/169357 A1 | 11/2013 |
| WO | 2015/081119 A1 | 6/2015 |

OTHER PUBLICATIONS

Zhang et al., Phase Behavior, Density, and Crystallization of Polyethylene in n-Pentane and in n-Pentane/CO2 at High-Pressures, Journal of Applied Polymer Science (2003), vol. 89, 2201-2209.

(Continued)

*Primary Examiner* — Frances Tischler
(74) *Attorney, Agent, or Firm* — Husch Blackwell LLP

(57) ABSTRACT

The invention provides a method, and apparatus, for determining the degree of separation (DOS) of a polymer solution into a polymer-rich stream and a solvent-rich stream, said method comprising the following: adding to a liquid-liquid separation vessel the polymer solution, which comprises a polymer, a solvent and an anti-solvent; separating the polymer solution into a polymer-rich stream and a solvent-rich stream; removing at least some the polymer-rich stream from at least one outlet P on the vessel, and measuring the actual solution density of this polymer-rich stream using at least one flow meter; removing at least some of the solvent-rich stream from at least one other outlet S on the vessel, and (Continued)

measuring the actual density of the solvent-rich stream using at least one flow meter; and wherein the degree of separation (DOS) is determined by the following equation (Eqn. 1):

DOS=[actual solution density (polymer-rich steam)−actual solution density (solvent-rich stream)]/[theoretical solution density (polymer-rich stream)−theoretical solution density (solvent-rich stream)]  (Eqn. 1).

9 Claims, 1 Drawing Sheet

(56) References Cited

U.S. PATENT DOCUMENTS

| | | |
|---|---|---|
| 9,018,328 B2 | 4/2015 | Jog et al. |
| 9,181,357 B2 | 11/2015 | Omicini |
| 2012/0277392 A1 | 11/2012 | Hypolite et al. |

OTHER PUBLICATIONS

Ehrlich et al., Phase Equilibria of Polymer-Solvent Systems at High Pressures Near Their Critical Loci: Polyethylene with n-Alkanes, Journal of Polymer Science (1963), Part A, vol. 1, 3217-3229.
De Loos et al, Liquid-liquid Phase Separation in Linear Low Density Polyethylene-Solvent Systems, Fluid Phase Equilibria (1996), 117(1-2), 40-7.
Buchelli et al., On-Line Liquid-Liquid Phase Separation Predictor in the High-Density Polyethylene Solution Polymerization Process, Industrial & Engineering Chemistry Research (2007), 46(12), 4307-4315.
Micro Motion Elite Coriolis Flow and Density Meters Product Data Sheet, Jul. 2010.
Proline Promass 80F,83F Coriolis Mass flow Measuring System, Technical Information, Feb. 2010.
PCT/US2014/067461, International Search Report and Written Opinion. dated Feb. 12, 2015.
PCT/US2014/067461, International Preliminary Report on Patentability. Report dated May 31, 2016.

\* cited by examiner

PROCESS AND APPARATUS TO DETERMINE THE DEGREE OF SEPARATION OF TWO SOLUTION STREAMS

REFERENCE TO RELATED APPLICATIONS

This application claims the benefit of U.S. Provisional Application No. 61/909442, filed Nov. 27, 2013, incorporated herein by reference.

BACKGROUND

A liquid-liquid separator is used in solution polymerizations to separate the solvent and unreacted monomers (in a solvent-rich stream) from the polymer (in a polymer-rich stream). The degree of separation is influenced by the process conditions, such as, for instance, the amount of anti-solvent (e.g., propane), the amount unreacted monomers in the inlet stream, the inlet stream temperature, and the adiabatic pressure drop into the separator. However, the degree of separation is typically not realized, until undesirable polymer carry over is detected in the solvent recovery downstream equipment. Thus, there is a need for a method to determine the degree of separation of solvent and unreacted monomers from the polymer, early on, in the "work-up process" of polymer solution, and which would allow for the on-line adjustment of polymerization conditions to improve the degree of separation.

Polymerization processes and/or polymer separation processes are disclosed in the following references: International Publications,WO2012/156393,WO2002/034795, WO2011/008955; US2012/0277392; Zhang et al., *Phase Behavior, Density, and Crystallization of Polyethylene in n-Pentane and in n-Pentane/CO2 at High Pressures*, Journal of Applied Polymer Science (2003), Vol. 89, 2201-2209; Ehrlich et al., *Phase Equilibria of Polymer-Solvent Systems at High Pressures Near Their Critical Loci: Polyethylene with n-Alkanes*, Journal of Polymer Science (1963), Part A, Vol. 1, 3217-3229; De Loos et al, *Liquid-liquid Phase Separation in Linear Low Density Polyethylene-Solvent Systems*, Fluid Phase Equilibria (1996), 117(1-2), 40-7; Buchelli et al., *On-Line Liquid-Liquid Phase Separation Predictor in the High-Density Polyethylene Solution Polymerization Process*, Industrial & Engineering Chemistry Research (2007), 46(12), 4307-4315.

However, the separation process of the above art does not allow for real time feedback of the degree of separation of the polymer solution into a polymer-rich stream and a solvent-rich stream. As discussed, there remains a need for a method to determine the degree of separation of solvent and unreacted monomers from the polymer, early on, in the work-up process of polymer solution, and which would allow for the on-line adjustment of polymerization conditions to improve the degree of separation. These needs have been met by the following invention.

SUMMARY OF INVENTION

A novel, non-intrusive technique has been developed to determine the degree of separation of two solutions, a polymer-rich stream and a solvent-rich stream. This technique utilizes flow meters (for example, coriolis meters) to measure the actual density of each stream (solvent-rich stream and polymer-rich stream) exiting a liquid-liquid separation vessel.

The invention provides a method for determining the degree of separation (DOS) of a polymer solution into a polymer-rich stream and a solvent-rich stream, said method comprising the following:

adding to a liquid-liquid separation vessel the polymer solution, which comprises a polymer, a solvent and an anti-solvent;

separating the polymer solution into a polymer-rich stream and a solvent-rich stream;

removing at least some the polymer-rich stream from at least one outlet P on the vessel, and measuring the actual solution density of this polymer-rich stream using at least one flow meter;

removing at least some of the solvent-rich stream from at least one other outlet S on the vessel, and measuring the actual density of the solvent-rich stream using at least one flow meter; and wherein the degree of separation (DOS) is determined by the following equation (Eqn. 1):

DOS=[actual solution density (polymer-rich steam)−actual solution density (solvent-rich stream)]/[theoretical solution density (polymer-rich stream)−theoretical solution density (solvent-rich stream)]     (Eqn. 1).

The invention also provides an apparatus for determining the degree of separation (DOS) of a polymer solution into a polymer-rich stream and a solvent-rich stream, said apparatus comprising at least the following;

a liquid-liquid separation vessel comprising at least one outlet P and at least one outlet S;

at least two flow meters; and wherein at least one flow meter is in contact with at least some of the polymer-rich stream that exits the vessel via outlet P; and wherein at least one other flow meter is in contact with at least some of the solvent-rich stream that exits the vessel via outlet S.

DETAILED DESCRIPTION

Figure 1:
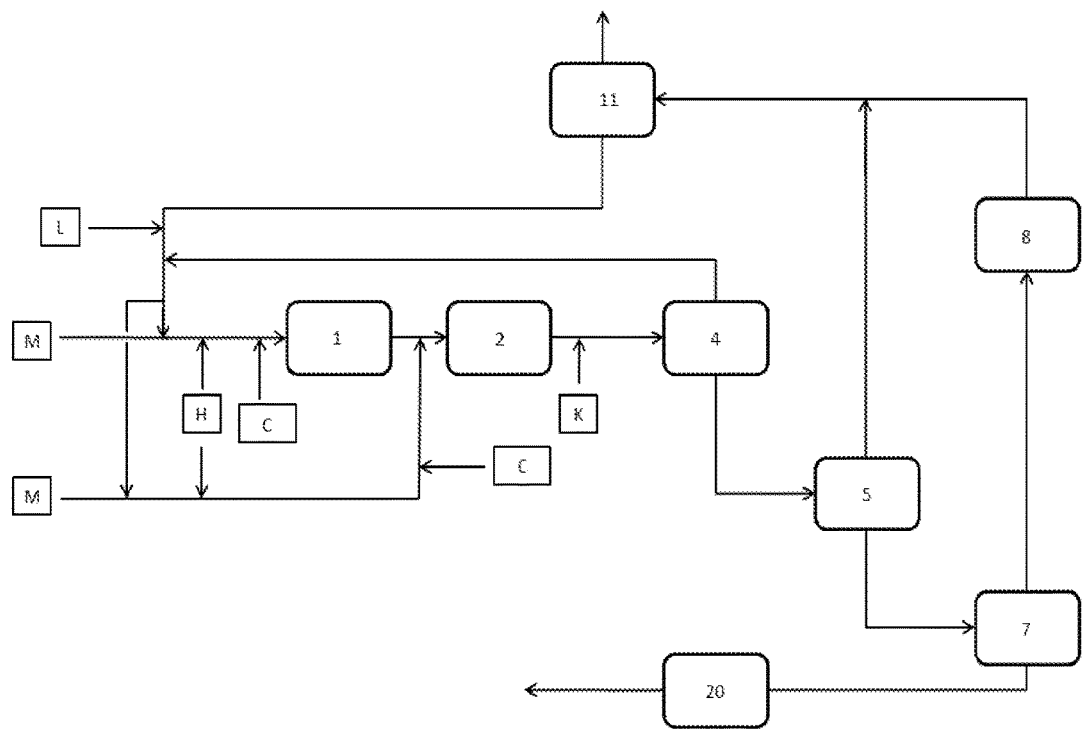
FIG. 1 depicts a solution polymerization process comprising an inventive apparatus used to determine the degree of separation (DOS) of a polymer solution into a polymer-rich stream and a solvent-rich stream. For example, the solution polymerization of EPDM, where [M]=ethylene, propylene, ENB, [H]=hydrogen, [C]=catalyst, [L]=anti-solvent, and [K]=catalyst-kill.

As discussed above, the invention relates a method for determining the degree of separation (DOS) of a polymer solution into a polymer-rich stream and a solvent-rich stream, said method comprising the following:

adding to a liquid-liquid separation vessel the polymer solution, which comprises a polymer, a solvent and an anti-solvent;

separating the polymer solution into a polymer-rich stream and a solvent-rich stream;

removing at least some the polymer-rich stream from at least one outlet P on the vessel, and measuring the actual solution density of this polymer-rich stream using at least one flow meter;

removing at least some of the solvent-rich stream from at least one other outlet S on the vessel, and measuring the actual density of the solvent-rich stream using at least one flow meter; and wherein the degree of separation (DOS) is determined by the following equation (Eqn. 1):

DOS=[actual solution density (polymer-rich steam)−
actual solution density (solvent-rich stream)]/
[theoretical solution density (polymer-rich
stream)−theoretical solution density (solvent-
rich stream)]     (Eqn. 1).

An inventive method may comprise a combination of two or more embodiments described herein.

In one embodiment, the theoretical solution density of the polymer-rich stream and the theoretical solution density of the solvent-rich stream are each determined using computer software for modeling asymmetric fluid systems. In a further embodiment, the computer software is a software for thermodynamic modeling of asymmetric fluid systems, and further a VLXE* software (for example, VLXE 4.5). See www.vlxe.com.

In one embodiment, the outlet P is located below the outlet S.

In one embodiment, the polymer is an olefin-based polymer.

In one embodiment, the polymer is selected from an ethylene-based polymer or a propylene-based polymer.

In one embodiment, the DOS is from 0.80 to 1.20, further from 0.85 to 1.15, further from 0.90 to 1.10, and further from 0.95 to 1.05.

In one embodiment, the polymer solution is separated into the polymer-rich stream and the solvent-rich stream by a reduction in the pressure in the liquid-liquid separation vessel. In a further embodiment, the pressure is reduced at a control rate.

The invention also provides an apparatus for determining the degree of separation (DOS) of a polymer solution into a polymer-rich stream and a solvent-rich stream, said apparatus comprising at least the following;

a liquid-liquid separation vessel comprising at least one outlet P and at least one outlet S;

at least two flow meters; and wherein at least one flow meter is in contact with at least some of the polymer-rich stream that exits the vessel via outlet P; and wherein at least one other flow meter is in contact with at least some of the solvent-rich stream that exits the vessel via outlet S.

An inventive apparatus may comprise a combination of two or more embodiments described herein.

In one embodiment, the degree of separation (DOS) is determined by the following equation (Eqn. 1):

DOS=[actual solution density (polymer-rich steam)−
actual solution density (solvent-rich stream)]/
[theoretical solution density (polymer-rich
stream)−theoretical solution density (solvent-
rich stream)]     (Eqn. 1).

In one embodiment, the DOS is from 0.90 to 1.10, and further from 0.95 to 1.05.

In one embodiment, the theoretical solution density of the polymer-rich stream and the theoretical solution density of the solvent-rich stream are each determined using a computer software for modeling asymmetric fluid systems. In a further embodiment, the computer software is a software for thermodynamic modeling of asymmetric fluid systems, and further a VLXE* software (for example, VLXE 4.5). See www.vlxe.com.

In one embodiment, the outlet P is located below the outlet S.

In one embodiment, the polymer is an olefin-based polymer.

In one embodiment, the polymer is selected from an ethylene-based polymer or a propylene-based polymer.

In one embodiment, the polymer solution comprises a polymer, a solvent and an anti-solvent.

In one embodiment, the polymer solution is separated into the polymer-rich stream and the solvent-rich stream in the liquid-liquid separation vessel, and further by a reduction in the pressure in the liquid-liquid separation vessel. In a further embodiment, the pressure is reduced at a control rate.

In one embodiment, the apparatus further comprises a pressure reducing means for reducing the pressure in the liquid-liquid separation vessel.

The following embodiments apply to both an inventive method and an inventive apparatus, as described above.

In one embodiment, the polymer solution comprises a polymer selected from an ethylene-based polymer or a propylene-based polymer. In a further embodiment, the polymer is an ethylene-based polymer. In yet a further embodiment, the concentration of ethylene fed to the reactor is less than 30 weight percent, preferably less than 20 weight percent, based on the weight of feed to the reactor, if only one reactor is used, or based on the weight of the feed to each reactor, if more than one reactor is used. In a further embodiment, the ethylene-based polymer is an ethylene/alpha-olefin interpolymer. In a further embodiment, the alpha-olefin is a C3-C8, preferably a C4-C8 alpha-olefin. In a further embodiment, the interpolymer contains less than 30 weight percent of the alpha-olefin, based on the weight of the interpolymer.

In one embodiment, the ethylene-based polymer is an EPDM.

Examples of solvents include, but are not limited to, hydrocarbons containing six or more carbon atoms, and mixtures of such hydrocarbons. Such a hydrocarbon solvent does not comprise a hydrocarbon containing less than six carbon atoms, although residual amounts (typically less than 10,000 ppm, based on total weight of the hydrocarbon solvent) of these hydrocarbons may be present. Typically, such hydrocarbon solvents have a normal boiling point higher than 95° C. A "hydrocarbon," as used herein refers to an organic molecule made up of only carbon and hydrogen atoms. Examples of solvents include n-octane, n-nonane, iso-octane, and alkenes like internal isomers of octene (those with double bond not located on a terminal carbon atom).

In one embodiment, the solvent comprises a hydrocarbon containing greater than, or equal to, 6 carbon atoms.

In one embodiment, the solvent is a hydrocarbon containing greater than, or equal to, 6 carbon atoms.

The solvent may comprise a combination of two or more embodiments described herein.

Examples of anti-solvents include, but are not limited to, hydrocarbons containing hydrocarbons containing five or less carbon atoms, and mixtures of such hydrocarbons. Such anti-solvents do not comprise a hydrocarbon containing more than five carbon atoms, although residual amounts (typically less than 10,000 ppm, based on total weight of the hydrocarbon anti-solvent) of these hydrocarbons may be present. Typically, such anti-solvents have a normal boiling point lower than 40° C. A "hydrocarbon," as used herein refers to an organic molecule made up of only carbon and hydrogen atoms. Examples of anti-solvents include ethane, propane, isobutene, and the like.

In one embodiment, the anti-solvent comprises a hydrocarbon containing less than 6 carbon atoms.

In one embodiment, the anti-solvent is a hydrocarbon containing less than 6 carbon atoms.

The anti-solvent may comprise a combination of two or more embodiments described herein.

In one embodiment, the anti-solvent comprises at least one hydrocarbon containing from 2 to 5 carbon atoms, further from 2 to 4 carbon atoms.

In one embodiment, the anti-solvent is selected from ethane, propane, isobutane, pentane or isopentane, or mixtures thereof, and further propane or isobutane.

In one embodiment, the solvent comprises at least one hydrocarbon containing from 6 to 10 carbon atoms, further from 7 to 9 carbon atoms.

In one embodiment, the solvent comprises at least one hydrocarbon containing from 7 to 10 carbon atoms, further from 8 to 10 carbon atoms, further from 9 to 10 carbon atoms.

In one embodiment, the solvent is selected from n-hexane, n-heptane, n-octane, iso-octane, n-nonane, n-decane, or mixtures thereof, further n-octane, iso-octane, n-nonane, n-decane, or mixtures thereof, and further n-octane.

In one embodiment, the solvent comprises a hydrocarbon with 6 or more carbon atoms, further 7 or more carbon atoms, further 8 or more carbon atoms.

In one embodiment, the solvent comprises a hydrocarbon with 8 or more carbon atoms, further 9 or more carbon atoms, more further 10 or more carbon atoms.

In one embodiment, the anti-solvent comprises a hydrocarbon with 5 or less carbon atoms, further 4 or less carbon atoms, more further 3 or less carbon atoms.

In one embodiment, the anti-solvent comprises a hydrocarbon with 4 or less carbon atoms, and the solvent comprises a hydrocarbon with 6 or more carbon atoms, further 7 or more carbon atoms, further 8 or more carbon atoms, further 9 or more carbon atoms.

In one embodiment, the anti-solvent comprises, as a majority weight percent, based on the weight of the anti-solvent, a hydrocarbon with 5 or less carbon atoms, further 4 or less carbon atoms, and the solvent comprises, as a majority weight percent, based on the weight of the solvent, a hydrocarbon with 6 or more carbon atoms, further 7 or more carbon atoms, further 8 or more carbon atoms, further 9 or more carbon atoms.

The anti-solvent may comprise a combination of two or more embodiments described herein.

The solvent may comprise a combination of two or more embodiments described herein.

In one embodiment, the amount of anti-solvent is from 5 to 40 weight percent, further from 10 to 35 weight percent, further from 15 to 30 weight percent, based on the weight of the polymerization system.

In one embodiment, the anti-solvent is present in an amount from 5 to 50 weight percent, further from 10 to 45 weight percent, and further from 15 to 40 weight percent, based on the weight of the solvent and the anti-solvent.

In one embodiment, the solvent is present in an amount from 50 to 95 weight percent, further from 55 to 90 weight percent, and further from 60 to 85 weight percent, based on the weight of the solvent and the anti-solvent.

In one embodiment, the anti-solvent is present in an amount from 10 to 40 weight percent, further from 15 to 35 weight percent, and further from 20 to 30 weight percent, based on the weight of the solvent and the anti-solvent.

In one embodiment, the solvent is present in an amount from 60 to 90 weight percent, further from 65 to 85 weight percent, and further from 70 to 80 weight percent, based on the weight of the solvent and the anti-solvent.

In one embodiment, the polymer concentration in the polymer rich stream is controlled by adjusting the amount of anti-solvent.

In one embodiment, there is no special unit operation (like distillation), in the polymerization process, to separate the solvent and anti-solvent.

In one embodiment, the polymer solution is formed in a polymerization that takes place in a reactor configuration selected from the group consisting of one of the following: (a) one reactor, and (b) two or more reactors configured in series. In a further embodiment, the each reactor in the reactor configuration does not contain a cooling system.

In one embodiment, each reactor in the reactor configuration is an adiabatic reactor.

In one embodiment, the pressure in each reactor is from 40 Bar (4 MPa) to 180 Bar (18 MPa), further from 60 Bar (6 MPa) to 160 Bar (16 MPa).

In one embodiment, the pressure in each reactor is from 90 Bar (9 MPa) to 180 Bar (18 MPa), further from 90 Bar (9 MPa) to 160 Bar (16 MPa).

In one embodiment, the pressure in each reactor is from 110 Bar (11 MPa) to 180 Bar (18 MPa), further from 110 Bar (11 MPa) to 160 Bar (16 MPa).

In one embodiment, each reactor operation temperature is greater than, or equal to, 130° C., further greater than, or equal to, 140° C., further greater than, or equal to, 150° C., and further greater than, or equal to, 160° C.

In one embodiment, the each reactor operation temperature is from 140° C. to 220° C., further from 150° C. to 210° C., further from 160° C. to 200° C.

In one embodiment, the polymerization is a continuous polymerization.

In one embodiment, the polymerization is a batch polymerization.

In one embodiment, the polymer concentration in the polymer solution entering the liquid-liquid separation vessel is from 10 to 50 weight percent, from 20 to 50 weight percent, from 30 to 50 weight percent, based on the weight of the polymer solution.

In one embodiment, no heat is added between each reactor and the liquid-liquid separation vessel.

In one embodiment, in the liquid-liquid separation vessel, the pressure is reduced to a pressure in the range from 80 Bar (8 MPa) to 10 Bar (1 MPa), preferably from 70 Bar (7 MPa) to 30 Bar (3 MPa).

In one embodiment, in the liquid-liquid separation vessel, the polymer solution forms only two liquid phases.

In a preferred embodiment, no phase separation agent is added to the polymer solution prior to, or within, the liquid-liquid separation vessel. In a further embodiment, no phase separation agent is added to the polymer-rich stream after the liquid-liquid separation vessel. Some examples of phase separation agents include H2, N2, CO, CO2, and CH4.

In one embodiment, the temperature in the liquid-liquid separation vessel is greater than, or equal to, 140° C., preferably greater than, or equal to, 160° C., and more preferably greater than, or equal to, 170° C.

In one embodiment, the temperature in the liquid-liquid separation vessel is less than, or equal to, 220° C., further less than, or equal to, 215° C., further less than, or equal to, 210° C., further less than, or equal to, 205° C.

In one embodiment, the temperature in the liquid-liquid separation vessel is from 140° C. to 220° C., further from 160° C. to 210° C., and further from 165° C. to 205° C.

In one embodiment, the liquid-liquid separation vessel has a capacity from 10 to 50,000 gallons.

In one embodiment, the liquid-liquid separation vessel has a capacity greater than, or equal to, 100 gallons.

In one embodiment, the liquid-liquid separation vessel has a capacity greater than, or equal to, 1,000 gallons.

In one embodiment, the liquid-liquid separation vessel has a capacity greater than, or equal to, 50,000 gallons.

In one embodiment, the liquid-liquid separation vessel has a capacity from 10 to 100 gallons.

In one embodiment, the liquid-liquid separation vessel has a capacity from 10 to 1,000 gallons.

In one embodiment, the liquid-liquid separation vessel has a capacity from 10 to 5,000 gallons.

In one embodiment, no mechanical mixing takes place in the liquid-liquid separation vessel.

In one embodiment, no sonic transponder is used inside the liquid-liquid separation vessel. In a further embodiment, no sonic transponder is not used downstream from the liquid-liquid separation vessel. In another embodiment, a sonic transponder is used downstream from the liquid-liquid separation vessel.

The liquid-liquid separation vessel may comprise a combination of two or more embodiments as described herein.

Examples of suitable flow meters include, but are not limited to, MICRO MOTION ELITE flow and density meters (for example, MICRO MOTION ELITE Coriolis meters), available from Emerson Process Management; and PROLINE PROMASS flow meters (for example, PROLINE PROMASS 80F, 83F Coriolis meters), available from Endress and Hauser.

DEFINITIONS

The term "polymer," as used herein, refers to a polymeric compound prepared by polymerizing monomers, whether of the same or a different type. The generic term polymer thus embraces the term homopolymer (employed to refer to polymers prepared from only one type of monomer, with the understanding that trace amounts of impurities may be incorporated into a polymer), and the term interpolymer as defined hereinafter. Trace amounts of impurities, such as catalyst residues, may be incorporated into or within a polymer.

The term "interpolymer," as used herein, refers to polymers prepared by the polymerization of at least two different types of monomers. The generic term interpolymer thus includes copolymers (employed to refer to polymers prepared from two different types of monomers), and polymers prepared from more than two different types of monomers.

The term "olefin-based polymer," as used herein, refers to a polymer that comprises at least a majority weight percent, based on the weight of the polymer, polymerized olefin (for example, ethylene or propylene), and, optionally, one or more additional comonomers.

The term "ethylene-based polymer," as used herein, refers to a polymer that comprises at least a majority weight percent polymerized ethylene (based on the weight of polymer), and, optionally, one or more additional comonomers.

The term "propylene-based polymer," as used herein, refers to a polymer that comprises at least a majority weight percent polymerized propylene (based on the weight of polymer), and, optionally, one or more additional comonomers.

The term "polymer-rich phase," as used herein, in relation to two or more phases under consideration, refers to the phase containing the greater concentration of polymer, as measured by its weight fraction, based on the total weight of the phase.

The term "solvent-rich phase," as used herein, in relation to two or more phases under consideration, refers to the phase containing the greater concentration of solvent, as measured by its weight fraction, based on total weight of the phase.

The term "polymer-rich stream," as used herein, in relation to two or more streams under consideration, refers to the stream containing the greater concentration of polymer, as measured by its weight fraction, based on the total weight of the stream.

The term "solvent-rich stream," as used herein, in relation to two or more streams under consideration, refers to the stream containing the greater concentration of solvent, as measured by its weight fraction, based on total weight of the stream.

A phase, as used herein, refers to is a region of space (a thermodynamic system), throughout which all physical properties of a material are essentially uniform. Examples of physical properties include density, index of refraction, and chemical composition.

A liquid-liquid phase is a combination of two separate liquid phases which are not miscible.

The term "liquid-liquid separation vessel (LLS)," as used herein, refers to a device used for the separation of two or more liquid phases. The separation results from the specific action, for example, a reduction in pressure, taken to induce two or more liquid phases.

The term "polymer solution," as used herein, refers to the complete dissolution of polymer in one or more solvents (typically much lower in molecular weight than polymer) to form a homogeneous (most often in liquid state) phase. The solution comprises the polymer solvent, and may also comprise anti-solvent, unreacted monomers and other residuals of the polymerization reaction.

The term "solvent," as used herein, refers to a substance (for example, a hydrocarbon (excluding monomer and comonomer)) that dissolves a species of interest, like a monomer and/or polymer, resulting in a liquid phase.

The term "anti-solvent," as used herein, refers to a substance, which, when added to an existing polymer solution, has the effect of lowering the Lower Critical Solution Temperature (LCST) at a given polymer weight fraction, and, in turn, reduces the compatibility between the solvent and the polymer.

Lower Critical Solution Temperature (LCST), as used herein, is defined as the temperature, above which, a solution of fixed composition, at a fixed pressure, separates into two liquid phases, and, below this temperature, the solution exists as a single liquid phase.

The term "solution polymerization," as used herein, refers to a polymerization process, in which the formed polymer is dissolved in the polymerization medium (for example a solvent or solvent/anti-solvent mixture), under the polymerization conditions (temperature and pressure).

The term "polymerization system," as used herein, refers to a mixture comprising monomers, solvent and catalyst, and which will undergo polymerization reaction under appropriate conditions. The polymerization system corresponds to the total feed to the reactor.

The term "adiabatic reactor," as used herein, refers to a reactor which has no active heat removal mechanism and no active heat addition mechanism.

The term "pressure reducing means," as used herein, refers to a device, such as a control valve, that allows reduction in pressure of a continuous stream of liquid or a fixed batch of liquid.

The phrase "actively reduced in a controlled manner," as used herein, refers to an action, such as the use of a control valve, to reduce pressure to a desired level, and at a desired rate.

The terms "comprising," "including," "having," and their derivatives, are not intended to exclude the presence of any additional component, step or procedure, whether or not the same is specifically disclosed. In contrast, the term, "consisting essentially of" excludes from the scope of any succeeding recitation any other component, step or procedure, excepting those that are not essential to operability. The term "consisting of" excludes any component, step or procedure not specifically delineated or listed.

EXPERIMENTAL

Representative Polymerization

A suitable process flow diagram of an example solution polymerization (e.g., EPDM) is shown in FIG. 1. In this schematic, one or two reactors [1, 2], each with no heat removal mechanism, is/are used in the polymerization. A control valve positioned downstream of the reactor, and before the liquid-liquid separation vessel (LLS), is used for pressure reduction. The liquid-liquid separator vessel (LLS) [4] is used for separating a polymer-rich stream and a solvent-rich stream. A first stage devolatilizer [5] is used for removing solvent from the polymer-rich stream by vaporization. A second stage devolatilizer [7] is used for additional solvent removal by operating near vacuum (5-30 mbar) conditions. The final polymer product, after subject to solvent removal (under vacuum), can be pelletized using a pelletization system [20].

This process configuration also comprises a vacuum system device [8], and a recycle solvent flash drum [11]. The solvent-rich stream exiting the LLS can be filtered through a filter to remove polymer particles.

The polymerization is carried out in one or more adiabatic reactors. The number of reactors depends on the polymer type and desired molecular weight distribution. The reactor pressure is typically from 40 Bar (4 MPa) to 150 Bar (15 MPa). The reactor operating temperature is typically from 140° C. to 190° C. The reaction solvent is a mixture of a solvent and an anti-solvent. Examples of suitable solvents include n-heptane, n-octane, n-decane, ISOPAR-E (mixture of C5-C10 alkanes), and the like. Examples of suitable anti-solvents include ethane, propane and isobutane. Typical anti-solvent concentrations are from 5 weight percent to 40 weight percent, based on the total weight of the polymerization system (includes, for example, monomers, solvent, anti-solvent; the polymerization system corresponds to the total feed to the reactor).

Figure 2:
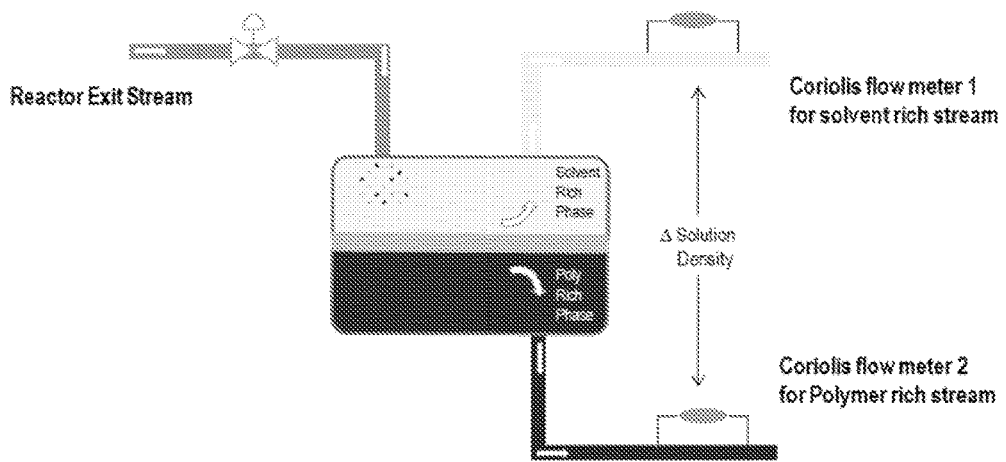
FIG. 2 is a schematic of an inventive apparatus used to determine the degree of separation (DOS) of a polymer solution into a polymer-rich stream and a solvent-rich stream.

Once the polymerization is completed, the polymer solution is transferred to the LLS [4]. The pressure in the LLS is reduced (for example, to 10~60 bar, depending on the initial pressure of the polymer solution entering the LLS) to induce a liquid-liquid separation, thus forming a polymer-rich phase and a solvent-rich phase. The polymer-rich phase is separated from the solvent-rich phase within the liquid-liquid separation vessel using gravity or an enhanced gravity device. The solvent-rich phase is separated, cooled, filtered, and recycled back to the reactor [1 and/or 2]. The actual solution densities of both the separated solvent-rich stream and the polymer-rich stream are measured by a pair of Coriolis flow meters, at the respective LLS exit stream, as shown in FIG. 2.

The polymer-rich phase is separated, passed through a heat exchanger, and then fed to the first devolatilizer [5]. A catalyst-kill [K] is added to the polymer-rich stream, before this stream enters the LLS, and further the first devolatilizer. The pressure in the first devolatilizer is reduced to form a polymer solution containing more than 50 weight percent polymer.

For final solvent removal, the concentrated polymer-rich stream, exiting the first devolatizer [5] is transferred to a second devolatizer [7]. Here, the pressure is reduced to form polymer with residual amounts (ppm levels) of solvent. The solvent coming out the second devolatizer is condensed, combined with solvent from first devolatizer, and the combined solvent is then purified, and then recycled back to the reactor [1 and/or 2]. The polymer is sent to a further material handling system, such as a pelletizer [20].

Degree of Separation (DOS)

As discussed above, once the polymerization is completed, the polymer solution is transferred to the LLS [4]. The actual solution densities of both the solvent-rich stream and the polymer-rich stream that exit the LLS are each measured by a Coriolis flow meter at the respective LLS exit stream, for example, as shown in FIG. 2.

The theoretical solution density of the solvent-rich stream and the theoretical solution density the polymer-rich stream are each determined using a computer software for thermodynamic modeling of asymmetric fluid systems, such as VLXE* software, VLXE 4.5. "VLXE 4.5" is a commercially available, thermodynamic program that uses algorithms to solve phase equilibrium equations for highly asymmetric systems, involving macromolecules and small molecule solvents (see www.vlxe.com).

The phase diagram calculation capability in the VLXE software allows calculation of phase boundaries, separating single phase, liquid-liquid, and vapor-liquid-liquid regions, for a given stream composition. The VLXE software can be used to determine the desired temperature and pressure that defines the boundaries of an asymmetric fluid system. The density results from two polymerizations are shown in Tables 1 and 2 below. Both polymerization were run, as described above, except that 15 weight percent propane was used in polymerization 1, and 20 weight percent propane was used in polymerization 2. The weight percent of propane (anti-solvent) was based on the total weight of the polymerization system (includes, for example, monomers, solvent, anti-solvent; the polymerization system corresponds to the total feed to the reactor). The solvent in each polymerization was ISOPAR-E.

The Degree of Separation (DOS) was determined using the following Equation 1:

DOS=[actual solution density (polymer-rich)−actual solution density (solvent-rich)]/ [theoretical solution density (polymer-rich)−theoretical solution density (solvent-rich)]  (Eqn. 1).

Each actual solution density was measured after the reading on each respective flow meter stabilized (about 40-60 minutes for a LLS vessel capacity of 25-30 gallons).

As the DOS approaches 1, the better the separation of the solvent from the polymer. The DOS was 1.05 and 0.98 for polymerizations (each EPDM) 1 and 2, respectively. These results indicate that excellent separation of the solvent from the polymer was achieved in the polymerizations using 15 weight percent and 20 weight percent propane.

TABLE 1

| Polymerization 1 using 15 wt % propane | | |
| --- | --- | --- |
| | Theoretical solution Density$^a$ (lb/ft$^3$) | Actual Solution Density (lb/ft$^3$) |
| Solvent-Rich | 28.7 | 30.3 |
| Polymer-Rich | 34.4 | 36.3 |
| Solution density Difference (polymer-rich − solvent rich) | 5.7 | 6.0 |

$^a$Determined using the VLXE software.

TABLE 2

| Polymerization using 20 wt % propane | | |
| --- | --- | --- |
| | Theoretical Solution Density$^a$ (lb/ft$^3$) | Actual Solution Density (lb/ft$^3$) |
| Solvent-Rich | 26.7 | 27.3 |
| Polymer-Rich | 35.5 | 35.9 |
| Solution density Difference (polymer-rich − solvent-rich) | 8.8 | 8.6 |

$^a$Determined using the VLXE software.

Although the invention has been described in considerable detail in the preceding examples, this detail is for the purpose of illustration, and is not to be construed as a limitation on the invention, as described in the following claims.

The invention claimed is:

1. A method for determining the degree of separation (DOS) of a polymer solution into a polymer-rich stream and a solvent-rich stream, said method comprising the following:

adding to a liquid-liquid separation vessel the polymer solution, which comprises a polymer, a solvent and an anti-solvent, the liquid-liquid separation vessel having no sonic transponder;

separating the polymer solution into a polymer-rich stream and a solvent-rich stream;

removing at least some the polymer-rich stream from at least one outlet P on the vessel, and measuring the actual solution density of this polymer-rich stream using a first flow and density meter at outlet P;

removing at least some of the solvent-rich stream from at least one other outlet S on the vessel, and measuring the actual density of the solvent-rich stream using a second flow and density meter at outlet S; and wherein the degree of separation (DOS) is determined by the following equation (Eqn. 1):

DOS =[actual solution density (polymer-rich steam) −actual solution density (solvent-rich stream)]/ [theoretical solution density (polymer-rich stream) −theoretical solution density (solvent-rich stream)]tm (Eqn. 1).

2. The method of claim 1, wherein the theoretical solution density of the polymer-rich stream and the theoretical solution density of the solvent-rich stream are each determined using computer software for modeling asymmetric fluid systems.

3. The method of claim 1, wherein the outlet P is located below the outlet S.

4. The method of claim 1, wherein the polymer is selected from an ethylene-based polymer or a propylene-based polymer.

5. The method of claim 1, wherein the solvent comprises a hydrocarbon containing greater than, or equal to, 6 carbon atoms.

6. The method of claim 1, wherein the anti-solvent is a hydrocarbon containing less than 6 carbon atoms.

7. The method of claim 1, wherein the DOS is from 0.90 to 1.10.

8. The method of claim 1 wherein the first flow and density meter is a Coriolis meter.

9. The method of claim 8 wherein the second flow and density meter is a Coriolis meter.

* * * * *